United States Patent [19]

Chen et al.

[11] Patent Number: 4,727,144

[45] Date of Patent: Feb. 23, 1988

[54] CERTAIN INTRACYCLIC OR EXTRACYCLIC PHOSPHOROUS CONTAINING COUMARINS USEFUL AS LASER DYES

[75] Inventors: Chin H. Chen, Webster, N.Y.; John L. Fox, Baltimore, Md.

[73] Assignee: Eastman Kodak Company, Rochester, N.Y.

[21] Appl. No.: 846,415

[22] Filed: Mar. 31, 1986

[51] Int. Cl.$^4$ .............................. C07F 9/38; C07F 9/65
[52] U.S. Cl. ...................................... 546/23; 549/216; 558/82
[58] Field of Search ................... 546/23, 21; 549/216; 558/82, 81

[56] References Cited

U.S. PATENT DOCUMENTS

| | | | |
|---|---|---|---|
| 3,221,027 | 11/1965 | Foster et al. | 549/220 |
| 3,772,340 | 11/1973 | Mhatre et al. | 549/220 |
| 3,876,666 | 4/1975 | Oswald et al. | 549/220 |
| 4,386,200 | 5/1983 | Fleck | 549/220 |

OTHER PUBLICATIONS

Singh et al., Journal of Heterocyclic Chemistry, vol. 22, No. 6, pp. 1713–1714, Nov.–Dec. 1985.

*Primary Examiner*—Alan L. Rotman
*Attorney, Agent, or Firm*—John R. Everett

[57] ABSTRACT

Phosphonocoumarins and phosphacoumarin lasing dyes are disclosed.

3 Claims, No Drawings

CERTAIN INTRACYCLIC OR EXTRACYCLIC PHOSPHOROUS CONTAINING COUMARINS USEFUL AS LASER DYES

FIELD OF THE INVENTION

This invention relates to novel organic laser dyes.

BACKGROUND OF THE INVENTION

Lasers (acronym for light amplification by stimulated emission radiation) or optical lasers (acronym for microwave amplification by stimulated emission radiation) are light amplifying devices which produce high intensity pulses of coherent monochromatic light concentrated in a well collimated beam commonly called a laser beam. There are several uses for such laser beams. Since the beam can be sharply focused, it can produce energy densities suitable for drilling, welding, cutting, etc. One potential application of laser beams is in the field of communications where the optical spectrum represents almost limitless bandwidth and information carrying capacity.

It is desirable to have lasers which are operable at many different wavelengths in the light spectrum including infrared, visible and ultraviolet regions. Since the wavelength emitted by a specific energy transition in a laser medium is tunable over only a small portion of the spectrum, it is necessary to provide a number of materials adapted for use as active laser media at various light frequencies. Certain organic dyes in solution can operate as "liquid" or "organic dye" lasers. Of the range of materials useful as lasing media, organic lasing dyes provide certain advantages. A wide range of organic dye lasers is available to provide stimulated emission (lasing) over a broad range of the spectrum. Secondly, organic dye lasers are generally capable of being tuned to emit over a range of wavelengths. Thirdly, organic dye lasers provide an economical lasing medium when compared to gas and solid lasers, and they do not suffer from disadvantages such as cracking and optical imperfections that are particularly associated with solid lasers.

The ability to selectively tune organic dye lasers derives from the broad band fluorescence characteristic of the dye. Such lasers can be "tuned" to emit at wavelengths along substantially the entire fluorescence band of the dye by interposing a dispersive element, such as a diffraction grating or a prism.

It is known that certain coumarin dyes are capable of lasing action. However, no coumarin dyes are known that include (1) a phosphorous atom in the coumarin ring, or (2) a phosphorous-containing substituent on the coumarin ring.

SUMMARY OF THE INVENTION

The present invention provides a novel compound selected from the group consisting of phosphonocoumarins and phosphacoumarins. These compounds are useful as lasing dyes as evidenced by their high quantum fluorescence.

In the compounds of this invention, the prefix "phosphono" indicates that the phosphorous is substituted outside the ring system. The prefix "phospha" indicates that the phosphorous is a part of the ring system.

Preferred lasing dyes of the invention have the structure

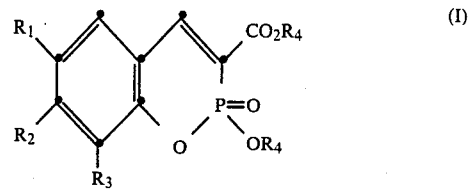

or

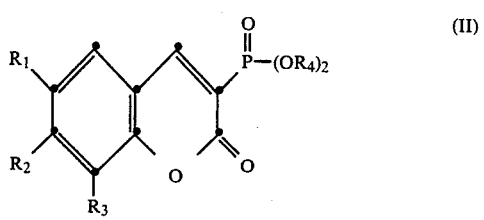

wherein
$R_1$, $R_2$ and $R_3$ each independently, represent hydrogen, alkyl such as methyl, ethyl, butyl and hexyl; alkoxy such as methoxy, ethoxy and pentoxy, or amino such as diethylamino; or $R_1$, $R_2$ and $R_3$ taken together with the atoms to which they are attached represent the necessary atoms and groups to constitute a multi fused ring group such as 2,3,8,9-tetrahydro-1H,7H-quinolizine; and $R_4$ represents alkyl such as described above for $R_1$, $R_2$ and $R_3$.

DETAILS OF THE INVENTION

The phosphono- and phosphacoumarins of this invention were made using commercially available salicylaldehydes and triethylphosphonoacetate as starting materials. The reaction involves a condensation/esterification procedure in which the starting materials are refluxed in a 10 mole percent solution of piperidinium acetate (Pip. HOAC) in toluene. The reaction scheme was:

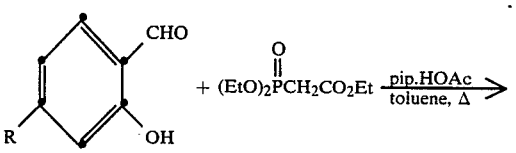

$$I + II \quad (1)$$

The mixtures of I and II were easily separated by flash chromatography. A non-limiting portion of the compounds of the invention are presented in Table I. Analytical data confirming the structure of the compounds is also presented. In Table I, the symbols Me and Et represent methyl and ethyl respectively.

TABLE I

| Compound No. | Structures | Molecular Formula | Combustion Analysis | | | | | |
|---|---|---|---|---|---|---|---|---|
| | | | Calcd. | | | Found | | |
| | | | C | H | N | C | H | N |
| 1. | (structure with MeO, CO₂Et, P(O)(OEt)) | $C_{14}H_{17}O_6P$ | 53.9 | 5.5 | 0 | 53.7 | 5.3 | 0 |
| 2. | (structure with MeO, P(OEt)₂) | $C_{14}H_{17}O_6P$ | 53.9 | 5.5 | 0 | 54.1 | 5.1 | 0 |
| 3. | (structure with Et₂N, CO₂Et, P(O)(OEt)) | $C_{17}H_{24}NO_5P$ | 57.8 | 6.8 | 4.0 | 57.5 | 6.8 | 3.8 |
| 4. | (structure with Et₂N, P(OEt)₂) | $C_{17}H_{24}NO_5P$ | 57.8 | 6.8 | 4.0 | 57.4 | 6.3 | 3.8 |
| 5. | (julolidine structure with CO₂Et, P(O)(OEt)) | $C_{17}H_{24}NO_5P$ | 60.5 | 6.4 | 3.7 | 60.7 | 6.2 | 3.4 |
| 6. | (julolidine structure with P(OEt)₂) | $C_{19}H_{24}NO_5P$ | 60.5 | 6.5 | 3.7 | 60.3 | 6.1 | 3.5 |

The spectra and quantum fluorescence property of the new dyes of Table I are given in Table II, infra. This data shows that the dyes have high fluorescence quantum efficiency and large Stokes' shift and would be useful in organic dye lasers.

The operation of a laser is achieved as a result of the phenomenon that excited atoms or molecules can emit a photon or quantum of light, which proton or quantum can itself trigger another excited atom or molecule to emit its photon prematurely. This process is designated stimulated emission. It is explained in U.S. Pat. No. 3,864,644.

Dye lasing is produced with a device having a reservoir means containing a laser dye solution and a pumping energy source capable of producing stimulated emission of the laser dye solution, the laser dye solution being a lasing concentration, in a non-interfering solvent, (i.e., one that does not inhibit stimulated emission, e.g., water, alkanols, etc.).

Dye solutions containing the novel dyes of the present invention can be used for lasing by employing conventional procedures, in any laser apparatus designed to employ liquid laser media, for example, the apparatus of Sorokin, mentioned in an article by Sorokin, Lankard, Moruzzi and Hammond, "Flashlamp-Pumped Organic Dye Lasers", *Journal of Chemical Physics*, Vol. 48.

It is generally accepted that among dyes of a particular class, those members having a higher fluorescence efficiency will be more susceptible of achieving stimulated emission under the proper conditions. Fluorescence efficiency is often meaningfully described in terms of fluorescence quantum yield. A quantum yield of 1.0 means that a quantum of fluorescent light is emitted for every quantum absorbed by the dye. Accordingly, the quantum yield is the ratio of emitted fluorescent light to absorbed light.

EXAMPLES 1-6

The following illustrative examples are included to show the quantum fluorescence of the dyes of the present invention. The dyes were made according to the condensation/esterification procedure mentioned hereinbefore. The determination of fluorescence quantum yield is conveniently accomplished according to recognized procedures, such as that described in Costa, Grum and Paine, "Absolute Luminescence Spectra via Digital-Technique and Time-Resolved Spectroscopy", *Applied Optics,* Vol. 8, June 1969, p. 1169; J. G. Calvert and J. N. Pitts, Jr., "Photochemistry", John Wiley and Sons, New York, NY, 1966, pp. 799–804; or C. A. Parker, "Photoluminescence of Solutions", Elsevier Publishing Co., Amsterdam, Netherlands, 1968, pp. 262–268.

The large Stokes' shift favors an increased lasing efficiency because of the decrease in overlap between the absorption and emission spectra.

TABLE II

| Compound | Example No. | Absorption $\lambda$-max(EtOH) | Fluorescence $\lambda$-max(EtOH) | A $\Delta_{\lambda\text{-}max}$ | F $-\lambda_{\lambda\text{-}max}$ | $\epsilon_a(cm^{-1}M^{-1})$ | $\Phi_f(\%)$ |
|---|---|---|---|---|---|---|---|
| 2 | 1 | 340 | 395 | 55 nm | | 17,750 | 16% |
| 1 | 2 | 332 | 395 | 63 nm | | 19,550 | 9% |
| 4 | 3 | 406 | 455 | 49 nm | | 34,500 | 4% |
| 3 | 4 | 400 | 457 | 57 nm | | 45,600 | 5% |
| 6 | 5 | 423 | 473 | 50 nm | | 36,600 | 70% |
| 5 | 6 | 420 | 478 | 58 nm | | 41,000 | 62% |

The invention has been described in detail with particular reference to preferred embodiments thereof, but it will be understood that variations and modifications can be effected within the spirit and scope of the invention.

We claim:

1. A compound selected from the group consisting of one having the following formulas

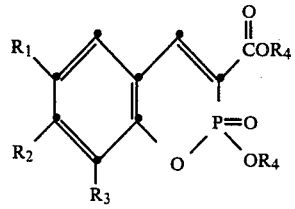

and

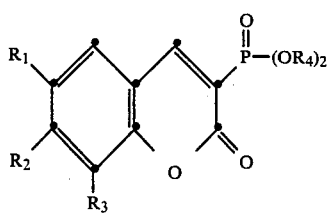

wherein $R_1$ and $R_3$ each independently represent hydrogen, methyl, ethyl, butyl or hexyl;

$R_2$ represents amino or diethylamino; or $R_1$, $R_2$ and $R_3$ taken together with the phenyl group to which they are attached provide the atoms necessary to form a fused 2,3,8,9-tetrahydro-1H,7H-quinolizine ring system;

$R_4$ represents methyl or ethyl.

2. A compound according to claim 1 wherein
$R_1$ and $R_3$ represents hydrogen;
$R_2$ represents diethylamino;
$R_4$ represents methyl or ethyl; or
$R_1$, $R_2$ and $R_3$, together with the phenyl group to which they are attached provide the atoms necessary to form a fused 2,3,8,9-tetrahydro-1H,7H-quinolizine ring system.

3. A compound according to claim 1 selected from those having the structure

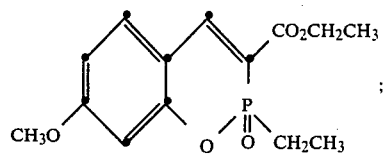

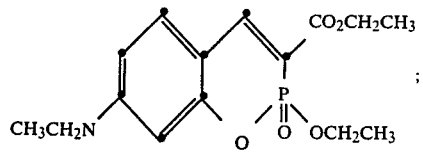

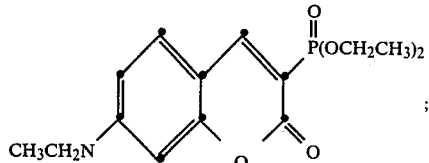

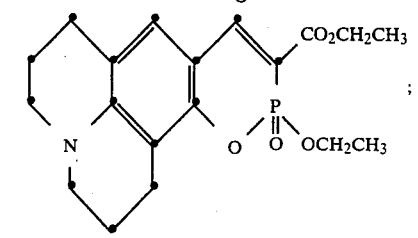

and

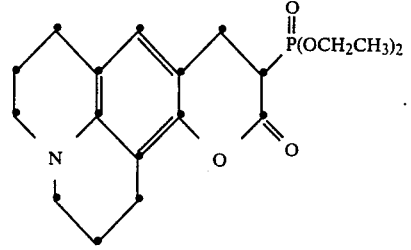

* * * * *